US012788357B2

(12) United States Patent
Cromwell

(10) Patent No.: US 12,788,357 B2
(45) Date of Patent: Nov. 10, 2026

(54) APPARATUS AND METHODS FOR PREDICTING IN VIVO FUNCTIONAL IMPAIRMENTS AND EVENTS

(71) Applicant: Entac Medical, Inc., Memphis, TN (US)

(72) Inventor: John W. Cromwell, Iowa City, IA (US)

(73) Assignee: Entac Medical, Inc., Memphis, TN (US)

( * ) Notice: Subject to any disclaimer, the term of this patent is extended or adjusted under 35 U.S.C. 154(b) by 154 days.

(21) Appl. No.: 17/339,919

(22) Filed: Jun. 4, 2021

(65) Prior Publication Data

US 2021/0378624 A1 Dec. 9, 2021

Related U.S. Application Data

(60) Provisional application No. 63/034,686, filed on Jun. 4, 2020.

(51) Int. Cl.

*A61B 7/00* (2006.01)
*A61B 5/00* (2006.01)
*G16H 50/20* (2018.01)

(52) U.S. Cl.

CPC ............ *A61B 7/008* (2013.01); *A61B 5/7257* (2013.01); *A61B 5/7267* (2013.01); *A61B 5/7275* (2013.01); *A61B 5/7475* (2013.01); *G16H 50/20* (2018.01)

(58) Field of Classification Search

CPC ..... A61B 7/008; A61B 5/7257; A61B 5/7267; A61B 5/7275; A61B 5/7475; A61B 5/42; A61B 5/0205; A61B 5/08; A61B 5/6852; A61B 5/7282; A61B 7/04; G16H 50/20; G16H 40/63; G16H 50/70; G10L 25/18

See application file for complete search history.

(56) References Cited

U.S. PATENT DOCUMENTS

| | | | |
|---|---|---|---|
| 5,140,994 | A | 8/1992 | Campbell et al. |
| 5,301,679 | A | 4/1994 | Taylor |
| 5,853,005 | A | 12/1998 | Scanlon |
| 6,056,703 | A | 5/2000 | Sandler et al. |
| 6,228,040 | B1 | 5/2001 | Craine |
| 6,287,266 | B1 | 9/2001 | Sandler et al. |

(Continued)

FOREIGN PATENT DOCUMENTS

| | | | |
|---|---|---|---|
| CN | 101541372 | | 9/2009 |
| CN | 102892349 | A | 1/2013 |

(Continued)

OTHER PUBLICATIONS

Chinese Search Report and English Language translation issued in related application No. CN 201180024426.5, dated Apr. 21, 2014.

(Continued)

*Primary Examiner* — Rene T Towa

(74) *Attorney, Agent, or Firm* — Arnall Golden Gregory LLP

(57) ABSTRACT

Methods, devices and systems for predicting non-clinical, undiagnosed conditions through audio data related to intestinal sounds of a patient or subject, wherein the methods, devices and systems utilize machine learning algorithms, and predicting the likelihood of in vivo impairment relative to the identified spectral events.

24 Claims, 2 Drawing Sheets

(56) References Cited

U.S. PATENT DOCUMENTS

| | | | | |
|---|---|---|---|---|
| 6,425,874 | B1 | 7/2002 | Sandler et al. | |
| 6,520,924 | B2 | 2/2003 | Lee | |
| 6,572,560 | B1 | 6/2003 | Watrous et al. | |
| 6,629,937 | B2 | 10/2003 | Watrous | |
| 6,776,766 | B2 | 8/2004 | Sandler et al. | |
| 6,840,913 | B2 | 1/2005 | Mansy et al. | |
| 7,187,790 | B2 | 3/2007 | Sabol et al. | |
| 8,715,201 | B2 | 5/2014 | Koehler et al. | |
| 9,179,887 | B2 | 11/2015 | Cromwell | |
| 9,402,596 | B1 | 8/2016 | Sheu et al. | |
| 10,603,006 | B2 | 3/2020 | Cromwell | |
| 11,801,030 | B2 | 10/2023 | Cromwell | |
| 11,918,408 | B2 | 3/2024 | Cromwell | |
| 2002/0052559 | A1* | 5/2002 | Watrous | A61B 7/00 600/528 |
| 2002/0058889 | A1 | 5/2002 | Lee | |
| 2002/0156398 | A1 | 10/2002 | Mansy et al. | |
| 2003/0018595 | A1* | 1/2003 | Chen | G06N 20/00 706/12 |
| 2004/0032957 | A1 | 2/2004 | Mansy et al. | |
| 2004/0122708 | A1 | 6/2004 | Avinash et al. | |
| 2006/0025650 | A1 | 2/2006 | Gavriely | |
| 2006/0167385 | A1* | 7/2006 | Guion | A61B 7/00 600/586 |
| 2007/0282174 | A1 | 12/2007 | Sabatino | |
| 2008/0235016 | A1 | 9/2008 | Paul et al. | |
| 2008/0306355 | A1 | 12/2008 | Walker | |
| 2010/0010358 | A1 | 1/2010 | Boute et al. | |
| 2010/0172839 | A1 | 7/2010 | Walker | |
| 2012/0156398 | A1 | 6/2012 | Kim | |
| 2012/0163622 | A1 | 6/2012 | Karthik et al. | |
| 2013/0035610 | A1 | 2/2013 | Cromwell | |
| 2013/0131532 | A1 | 5/2013 | Umana | |
| 2014/0276150 | A1 | 9/2014 | Sun et al. | |
| 2015/0011912 | A1 | 1/2015 | Matsuoka et al. | |
| 2015/0073306 | A1 | 3/2015 | Abeyratne et al. | |
| 2015/0119758 | A1 | 4/2015 | Rogers et al. | |
| 2015/0157273 | A1* | 6/2015 | An | A61B 5/7275 600/595 |
| 2015/0250445 | A1* | 9/2015 | Spiegel | A61B 5/0816 600/595 |
| 2016/0089107 | A1 | 3/2016 | Cromwell | |
| 2016/0354053 | A1* | 12/2016 | Tsai | A61B 5/7267 |
| 2016/0367823 | A1 | 12/2016 | Cowan et al. | |
| 2017/0050006 | A1 | 2/2017 | Imran et al. | |
| 2017/0340306 | A1 | 11/2017 | Spiegel et al. | |
| 2018/0078195 | A1 | 3/2018 | Sutaria et al. | |
| 2018/0271435 | A1 | 9/2018 | Zhao et al. | |
| 2018/0296092 | A1 | 10/2018 | Hassan et al. | |
| 2018/0303413 | A1 | 10/2018 | Hassan et al. | |
| 2019/0216420 | A1 | 7/2019 | Hsu et al. | |
| 2019/0374149 | A1* | 12/2019 | Wahlberg | A61B 7/02 |
| 2020/0060604 | A1 | 2/2020 | Mohammadi et al. | |
| 2020/0330066 | A1 | 10/2020 | Cromwell | |
| 2021/0000442 | A1 | 1/2021 | Marchall et al. | |
| 2021/0338154 | A1* | 11/2021 | Abeyratne | A61B 5/7253 |

FOREIGN PATENT DOCUMENTS

| | | | |
|---|---|---|---|
| CN | 104305961 | A | 1/2015 |
| CN | 104321015 | A | 1/2015 |
| CN | 106251880 | A | 12/2016 |
| EP | 0951867 | A2 | 10/1999 |
| EP | 1956982 | | 1/2015 |
| JP | 2005-027804 | A | 2/2005 |
| JP | 2008139447 | | 6/2008 |
| JP | 2010-282366 | A | 12/2010 |
| JP | 2016-36637 | A | 3/2016 |
| JP | 2020-511206 | A | 4/2020 |
| JP | 2020-515313 | A | 5/2020 |
| KR | 10-2012-0061780 | | 6/2012 |
| RU | 2145426 | | 2/2000 |
| RU | 2010153388 | A | 7/2012 |
| RU | 2539994 | C1 | 1/2015 |
| TW | 200706160 | | 2/2007 |
| WO | WO-97/36543 | | 10/1997 |
| WO | 2006/078954 | | 7/2006 |
| WO | WO-2007/107908 | | 9/2007 |
| WO | WO-2007/147049 | A2 | 12/2007 |
| WO | WO-2008/063938 | | 5/2008 |
| WO | WO-2009/074985 | | 6/2009 |
| WO | WO-2011/049293 | | 4/2011 |
| WO | 2011/113070 | | 9/2011 |
| WO | WO-2011/130589 | | 10/2011 |
| WO | WO-2012/057406 | | 5/2012 |
| WO | WO-2012/162740 | | 12/2012 |
| WO | WO-2014/039404 | | 3/2014 |
| WO | WO-2016206704 | A1 * | 12/2016 |
| WO | 2017/135127 | | 8/2017 |
| WO | WO-2018/011631 | | 1/2018 |
| WO | WO-2019/067880 | | 4/2019 |
| WO | 2019/216320 | A1 | 11/2019 |
| WO | WO-2019/241674 | | 12/2019 |
| WO | 2020/077413 | A1 | 4/2020 |
| WO | 2020/214866 | | 10/2020 |
| WO | 2021/248092 | | 12/2021 |

OTHER PUBLICATIONS

Dalle et al., "Computer analysis of bowel sounds," Computers in Biology and Medicine, 1974; 4, pp. 257-256.

European Search Report issued in related application No. EP 11769638.5, issued Jul. 18, 2014.

First Examination Report issued by the Intellectual Property Office in India for related Indian Application No. 9563/CHENP/2012, mailed Jul. 19, 2019.

Garner et al., "Non-invasive Topographic Analysis of Intestinal Activity in Man on the Basis of Acustic Phenomena," Res Exp Med., 1989; 189; pp. 129-140.

International Search Report and Written Opinion mailed Jul. 27, 2020 in International Patent Application No. PCT/US20/28600.

Sugrue et al., "Computerized Phonoenterography: The Clinical Investigation of a New System," Journal of Clinical Gastroenterology, 1994; 18(2): pp. 139-144.

Tomomasa et al., "Analysis of Gastrointestinal Sounds in Infants With Pyloric Stenosis Before and After Pyloromyotomy," [online], Pediatrics, 1999: 104(5), pp. 1-4. Retrieved from the Internet: < URL: http://www.pediatrics.org/cgi/content/full/104/5/e60>, provided by University of Iowa Hospitals on Jan. 1, 2010.

Tomomasa et al., "Gastrointestinal Sounds and Migrating Motor Complex in Fasted Humans," The American Journal of Gastroenterology, 1999; 94(2), pp. 374-381.

Watson et al., "Phonoenterography: the recording and analysis of bowel sounds," Gut, 1967; 8(88), pp. 88-94.

Yong et al., "The study of Intestinal Sound Analyzer," Journal of Electronic Measurement and Instrument, 1995; 9(1), with English language translation, translated by Morningside Translations on Nov. 3, 2014, 14 pages total.

International Search Report and Written Opinion issued in PCT/US2021/036037, mailed Sep. 9, 2021.

Search Report issued in Russian Patent Application No. 2021 133 022, dated Aug. 21, 2023.

U.S. Appl. No. 16/851,085, filed Apr. 16, 2020, U.S. Pat. No. 11,918,408, Mar. 5, 2024, Cromwell.

U.S. Appl. No. 18/595,932, filed Mar. 5, 2024, US 2024-0197283, Jun. 20, 2024, Cromwell.

U.S. Appl. No. 62/834,906, filed Apr. 16, 2019, Cromwell.

U.S. Appl. No. 63/034,686, filed Jun. 4, 2020, Cromwell.

PCT/US2020/028600, Apr. 16, 2020, WO 2020/214866, Oct. 22, 2020, Entac Medical, Inc.

PCT/US2021/036037, Jun. 4, 2021, WO 2021/248092, Dec. 9, 2021, Entac Medical, Inc.

Chinese Search Report and First Office Action with English Language translation issued in CN 202080029144.3, mailed Jul. 26, 2023.

Chinese Search Report and second Office Action with English Language translation issued in CN 202080029144.3, mailed Apr. 26, 2024.

(56) References Cited

OTHER PUBLICATIONS

European (Supplementary) Search Report and European Search Opinion issued in EP 20791291.6, mailed Dec. 12, 2022.
European (Supplementary) Search Report and European Search Opinion issued in EP 21818268.1, mailed Apr. 22, 2024.
European Rule 71(3) EPC Intention to Grant with a copy of the text proposed for grant issued in EP 20791291.6, mailed Apr. 17, 2024.
Japanese First Office Action and Search Report with English Language translation issued in JP 2021-561723, mailed Jan. 30, 2024.
Russian Office Action issued in RU 2021 133 022, with partial English translation, mailed Mar. 1, 2024.
Chinese Office Action with foreign counsel Brief Summary of second OA issued in CN 202180047719.9, mailed Feb. 5, 2026.
Japanese Office Action with machine translation issued in JP 2022 574809, mailed Mar. 3, 2026.

* cited by examiner

APPARATUS AND METHODS FOR PREDICTING IN VIVO FUNCTIONAL IMPAIRMENTS AND EVENTS

CROSS-REFERENCE TO RELATED APPLICATIONS

This Application claims the benefit of U.S. Provisional Application 63/034,686 filed on Jun. 4, 2020. The entire contents of this application is incorporated herein by reference in its entirety.

FIELD OF THE INVENTION

The invention generally relates to non-clinically and undiagnosed in vivo impairments, e.g., gastrointestinal conditions and impairments, and more specifically to predictive and preventative strategies of the same.

BACKGROUND OF THE INVENTION

Gastrointestinal intolerance or impairment (GII) can be defined as vomiting, requirement for nasogastric tube placement, or requirement for reversal of diet beyond 24 hours and less than 14 days following surgery. It is most commonly caused by postoperative ileus (POI). POI is acute paralysis of the GI tract that develops 2-6 days after surgery causing unwanted side-effects such as nausea and vomiting, abdominal pain and distention. This occurs most frequently in gastrointestinal surgery. The in vivo environment of a patient generates various sounds, which can be associated with certain physiological functions. In addition to GII, other potential life-threatening condition include, for example, congestive heart failure ("CHF"), acute respiratory distress syndrome ("ARDS"), pneumonia, pneumothoraxes, vascular anastomoses, arterial aneurysm, and the other similar conditions, for which internal sounds related to the specific condition can be collected for analysis as described herein and used to prevent, limit and/or prepare for life-threatening event predicted by the invention.

SUMMARY OF THE INVENTION

Certain embodiments of the present invention provide devices and systems for predictive assessment of potential life-threatening conditions related to gastrointestinal impairments, congestive heart failure ("CHF"), acute respiratory distress syndrome ("ARDS"), pneumonia, pneumothoraxes, vascular anastomoses, arterial aneurysm, and the other similar conditions, for which internal sounds related to the specific condition can be collected for analysis as described herein and used to prevent, limit and/or prepare for life-threatening event predicted by the invention. One embodiment of the invention is to predict, through analysis of intestinal sounds, the likelihood of a subject developing gastrointestinal intolerance or impairment following surgery. In other embodiments, the prediction of an intolerance or impairment is before there are any clinical or diagnosed symptoms of such an intolerance or impairment. In various embodiments, certain methods of the present invention utilize machine learning, wherein a machine learning encoder (e.g., an auto-encoder) and a machine learning classifier (e.g., an auto-classifier) are employed as part of a computer-implemented method, e.g., as part of an appropriate device and/or system, adapted to provide predictive assessment of potential life-threatening conditions as disclosed herein. In certain embodiments, there is a computer-implemented method for of providing real time improved predictive values for likelihood of an in vivo impairment or event occurring prior to clinical diagnosis and clinical symptoms.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE INVENTION

In an example of the present invention, an embodiment of the invention is used, wherein a machine learning algorithm of the invention is trained from 4-minute intestinal audio samples from subjects within 12 hours after major surgery. Audio samples can be collected, for example, by systems and devices as disclosed herein. In this example, the 4-minute intestinal audio samples were samples from subjects that experienced post-operative, subsequent outcomes with respect to GII. The 4-minute intestinal audio data is segregated randomly into training data (76%) (e.g., labeled audio samples) and test data (24%) (e.g., unlabeled audio samples) in the example below. Methods and equipment for obtaining the 4-minute intestinal audio samples are known and will be appreciated by those of ordinary skill in the art. For example, PrevisEA, which is noninvasive technology for detecting a biological signal (e.g., sound) that is highly correlated with the development of GII, has demonstrated high accuracy in the risk stratification of patients with 95 percent specificity and 83 percent sensitivity in the clinical setting. Moreover, the machine learning algorithm of an embodiment of the present invention can be implemented through a device (e.g., computer-implemented) such as the PrevisEA and related products as disclosed in WO2011/130589, U.S. Pat. Nos. 9,179,887 6and 10,603,006 and in U.S. Patent Application Publication No. 2020/0330066 (each of which is incorporated herein in its entirety by reference), and thereby using the structured system of components in the device to achieve the goals of enhanced predictive likelihoods of GII occurring in patients with no pre-clinical diagnosed symptoms of GII. As will be appreciated by those in the field, embodiments of the present invention can be implemented with such systems to predict the likelihood of other in vivo events based on signals determined to be related to the different medical conditions and future events.

Figure 1:
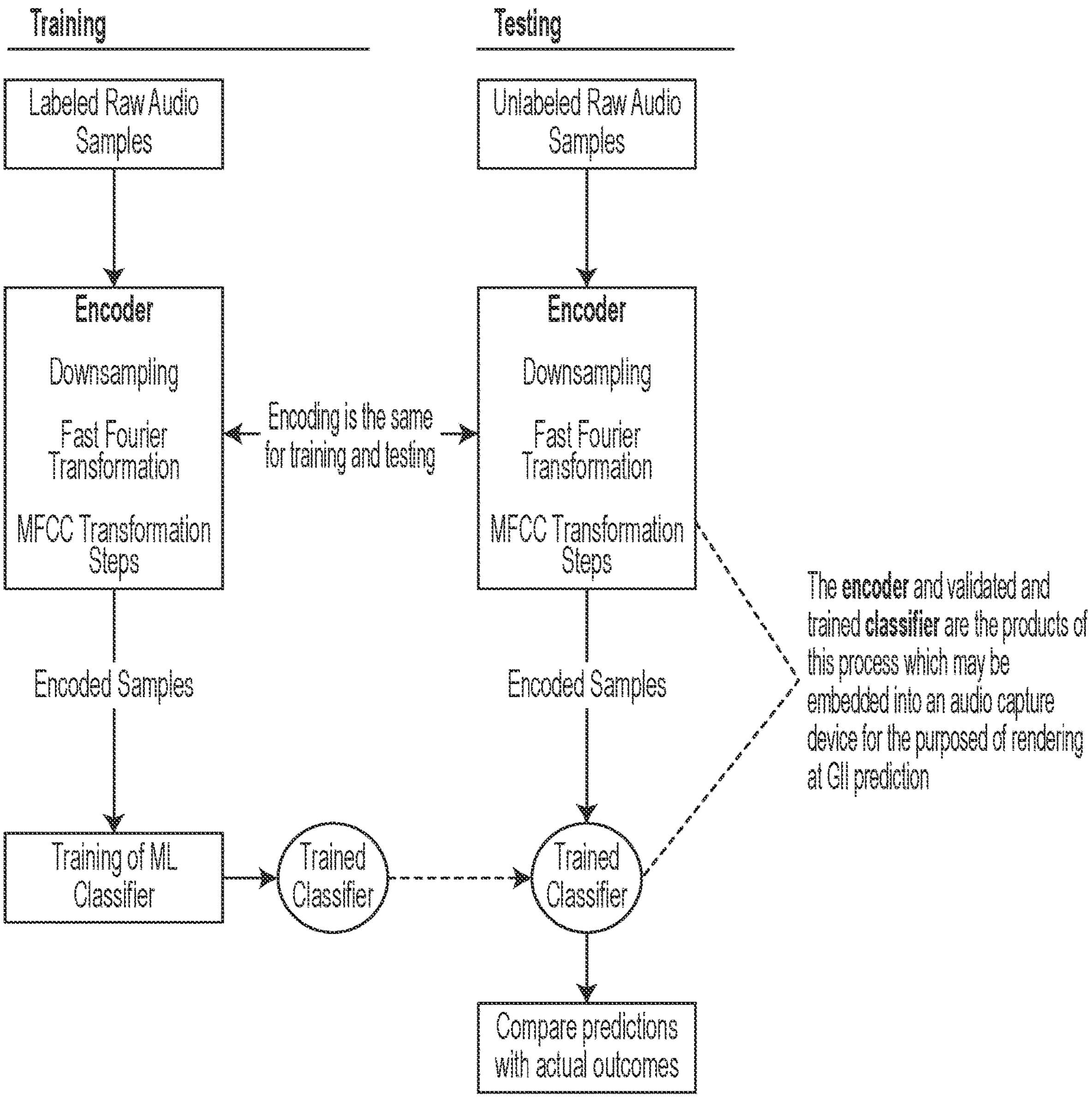
FIG. 1 is a flow diagram of one embodiment of the invention regarding certain aspects of the training and testing related to the algorithm.

As seen in the flow diagram of FIG. 1, labeled audio samples are used during training to create the machine learning components, e.g., an encoder component and a resulting classifier component; each component functions as part of the machine learning algorithm to then be evaluated for performance in the testing phase. The components generated during training then have the performance evaluated by performing analysis on the unlabeled test set. The products of this two-phased process are the two validated machine learning components of the algorithm. Also, as will be appreciated, certain embodiments of the present invention can be used with different machine learning approaches, e.g., supervised learning (e.g., using a set of data containing both inputs and desired outputs to build a mathematical model), unsupervised learning (e.g., learning from unlabeled test data, wherein the algorithm identifies commonalities in data and responds to presence or absence of such commonalities in each new piece of data).

Training the Algorithm

1. Each training sample gets passed through an encoder which transforms the data into a new representation of the data. This serves to reduce the dimensionality of the data and preserve data important for subsequent classification. As an example of dimensionality, a 4-minute sample can comprise more than a million discrete data points in the audio file. An encoder of the present invention can minimize the discrete data points to those data points of relevance to the predictive likelihood; thereby providing a smaller, focused fraction of discrete data points of relevance to the outcome. This aspect of the algorithm and the system within which it functions, reduces the time required for the analysis of data sets. The encoder transformations occur as follows:
   - A. Fast Fourier Transform (FFT), which is an algorithm, e.g., Cooley-Turkey, which converts a signal from its original domain (often time or space) to a representation in the frequency domain and vice versa.
   - B. Further transformation of post-FFT samples (e.g., for sound related sample)
     - i. mapping power spectrum obtained in step 1, e.g., onto the mel scale (i.e., using triangular overlapping windows)
     - ii. take the logs of the power at each of the mel frequencies
     - iii. take the discrete cosine transform of the list of mel log powers
     - iv. obtain the amplitudes of each resulting spectrum; these steps transform raw signal into the mel-frequency cepstral coefficients (MFCC) that markedly reduce the dimensionality of the data.
2. The encoded and labeled samples from step 4 are then passed through a machine learning classifier algorithm to generate the classifier function. Misclassification cost algorithms or up-sampling of rare classes may be applied during training to solve class imbalance issues. By way of non-limiting example, a class imbalance refers to a situation where one of the outcomes is rarely represented in the dataset. For instance, if GII occurred in only 1 of 100 patients, the simplest way for the algorithm to address this is to predict negative for all patients. As will be understood, this is not a desired characteristic of the system. Thus, if an "algorithmic cost" is introduced for having a false negative prediction, then the algorithm is then forced to make some positive predictions to find the 1 in 100. By way of non-limiting example, up-sampling of rare classes are duplicated multiple times in the training sample in such a way to force the training process to weight them more in the classifier. For example, if GII occurs in 1 out of 100 cases, one aspect of the invention can duplicate that one positive case 19 times so that class is now represented in 20 out of 119 cases in the training data. Again, this forces the classifier to increase the weighting of the GII positive cases. Numerous machine learning algorithms may be screened during this process and the best performing algorithm retained, for example, support vector machine, random forest, neural network, Naive Bayes, and many others.

Testing the Algorithm

1. Each testing sample is passed through the same encoder defined during training
2. Each unlabeled test sample is then classified using the classifier function generated in training above.
3. The predicted outcome is compared to the actual outcome to measure performance. An objective of this embodiment is to minimize false negatives and false positives.

As will be appreciated, an algorithm working within a system of the invention works by adjusting the classifier during the process. There is a need for a probability threshold, e.g., above is a yes, and below is a no; thus, different values or costs are assigned as would relate to the effect of a false reading. In one aspect of the invention, neural network perceptrons (an algorithm for supervised learning of a binary classifier) have their respective weights and biases iteratively adjusted in response to an error gradient in a process of stochastic gradient descent. In one aspect, an upper limit can be set on the number of times an algorithm may adjust. In other embodiments of the invention, multi-class perceptrons can be employed where the linear or binary perceptrons are not as useful, e.g., where the there is a need to classify instances into one of three or more classes.

Summary of Test Data

Using the above strategy, 68 labeled samples were used to train the algorithm and 22 unlabeled samples were used to test the algorithm. The classification performance on the test set was as follows:

n=22
Accuracy: 0.95
Sensitivity: 0.86
Specificity: 1.00
PPV: 1.00
NPV: 0.94
AUC: 0.91

Products of Training and Testing

The validated and trained encoder and validated and trained classifier are the products of this process which may be embedded into an audio capture device for the purpose of rendering a GII prediction. As will be appreciated, various computer forms can be used for the training and testing phases. For example, certain computer forms may comprise: a processor(s), motherboard, RAM, hard disk, GPU (or other alternatives such as FPGAs and ASIC), cooling components, microphone(s), a housing, wherein sufficient processing capacity and speeds, storage space and other requirements are provided to achieve the goals of the embodiments of the invention.

Figure 2:
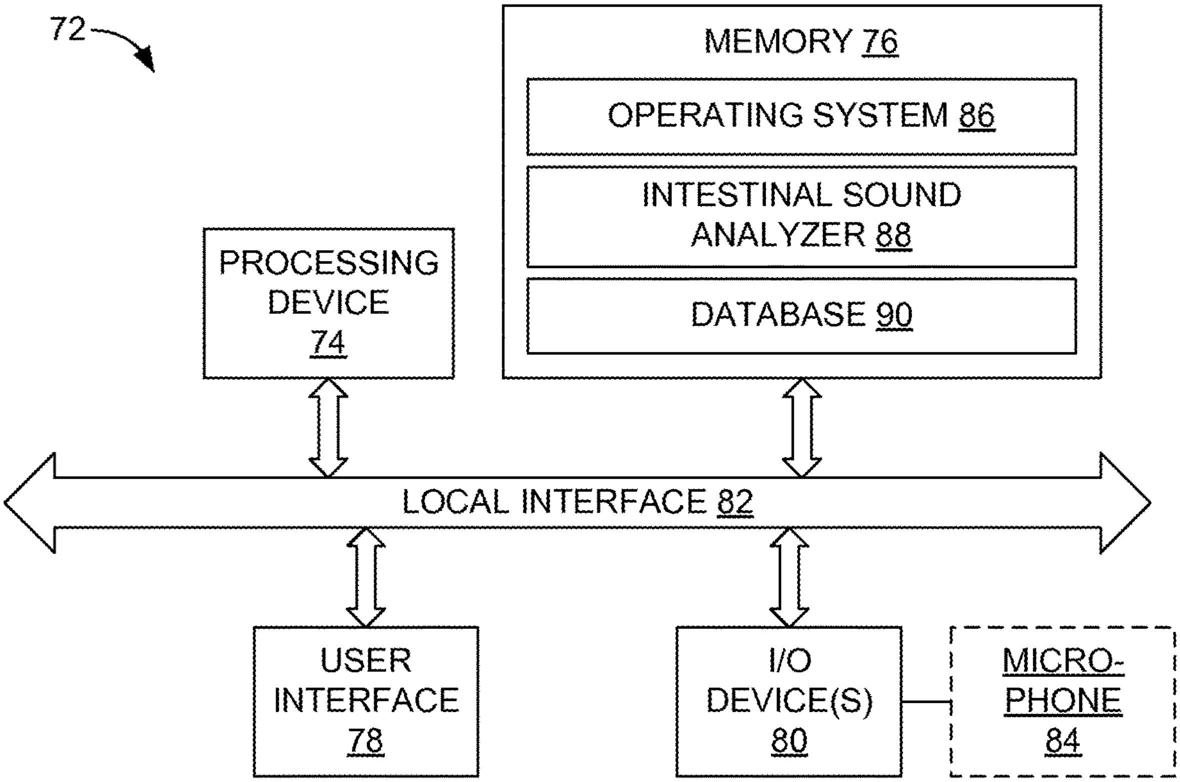
FIG. 2 is a block diagram of an embodiment of an architecture of a device that can process collected patient data to assist in the gastrointestinal impairment prediction and risk assessment.

As provided herein and illustrated in FIG. 2, embodiments of the present invention can be part of a device or certain systems of devices. A machine learning algorithm of the present invention can be implemented into a device such as the PrevisEA and/or related products as disclosed in WO2011/130589, U.S. Pat. Nos. 9,179,887 and 10,603,006 and in U.S. Patent Application Publication No. 2020/0330066 (each of which is incorporated herein in its entirety), and thereby using the structured system of components in the device to achieve the goals of enhanced predictive likelihoods of GII occurring in patients with no pre-clinical diagnosed symptoms of GII.

FIG. 2 illustrates an example architecture for a device 72 that can be used in a system for predicting gastrointestinal impairment to analyze collected patient data. By way of example, the architecture shown in FIG. 2 can be an architecture of a computer, a data collection device, a patient interface and/or patient monitoring system. Moreover, it is noted that the illustrated architecture can be distributed across one or more devices.

A system for use in conjunction with the algorithm of the embodiments of the invention generally comprise a data collection device, a patient interface, and a computer. The data collection device can comprise any device that is capable of collecting audio data that is generated within a patient's intestinal tract. In some embodiments, the data collection device comprises a portable (e.g., handheld) digital audio recorder. In such a case, the data collection device can comprise an integral microphone that is used to capture the intestinal sounds.

The patient interface is a device that can be directly applied to the patient's abdomen (or other body parts based on the application of the disclosed system) for the purpose of picking up intestinal sounds. In some embodiments, the patient interface comprises, or is similar in design and function to, a stethoscope head. Stethoscope heads comprise a diaphragm that is placed in contact with the patient and that vibrates in response sounds generated within the body. Those sounds can be delivered to the microphone of the data collection device via tubing that extends between the patient interface and the data collection device. Specifically, acoustic pressure waves created from the diaphragm vibrations travel within an inner lumen of the tubing to the microphone. In some embodiments, all or part of the patient interface can be disposable to avoid cross-contamination between patients. Alternatively, the patient interface can be used with a disposable sheath or cover that can be discarded after use.

The audio data collected by the data collection device can be stored within internal memory of the device. For example, the audio data can be stored within nonvolatile memory (e.g., flash memory) of the device. That data can then be transmitted to the computer for processing. In some embodiments, the data is transmitted via a wire or cable that is used to physically connect the data collection device to the computer. In other embodiments, the data can be wirelessly transmitted from the data collection device to the computer using a suitable wireless protocol such as Bluetooth or Wi-Fi (IEEE 802.11).

The computer can, in some embodiments, comprise a desktop computer. It is noted, however, that substantially any computing device that is capable of receiving and processing the audio data collected by the data collection device can be used in conjunction with the algorithms and embodiments of the invention. Therefore, the computer can, alternatively, take the form of a mobile computer, such as a notebook computer, a tablet computer, or a handheld computer. It is further noted that, although the data collection device and the computer disclosed as comprising separate devices, they can instead be integrated into a single device, for example a portable (e.g., handheld) computing device. For example, the data collection device can be provided with a digital signal processor and appropriate software/firmware that can be used to analyze the collected audio data.

In another embodiment, the patient interface can comprise a device having its own integral microphone. In such a case, patient sounds are picked up by the microphone of the patient interface and are converted into electrical signals that are electronically transmitted along a wire or cable to a data collection device for storage and/or processing. Alternatively, the patient sounds can be transmitted to the data collection device wirelessly. In some embodiments, the patient interface has an adhesive surface that enables the interface to be temporarily adhered to the patient's skin in similar manner to an electrocardiogram (EKG) lead. As with the previous embodiment, patient data can be transmitted from the data collection device to the computer via a wired connection (via wire or cable) or wirelessly.

In yet another embodiment, the data collection device comprises a component that is designed to dock with a patient monitoring system, which may be located beside the patient's bed. Such patient monitoring systems are currently used to monitor other patient parameters, such as blood pressure and oxygen saturation. In this embodiment, the patient monitoring system comprises a docking station and an associated display. In such a case, the data collection device can dock within a free bay of the station prior to use.

In some embodiments, the data collection device comprises no internal power supply and therefore can only collect patient data when docked. By way of example, the data collection device can have electrical pins that electrically couple the device to the patient monitoring system for purposes of receiving power and transferring collected data to the patient monitoring system. The patient data can then be stored in memory of the patient monitoring system and/or can be transmitted to a central computer for storage in association with a patient record in an associated medical records database.

The data collection device can comprise an electrical port that can receive a plug of the wire or cable. In addition, the data collection device can comprise one or more indicators, such as light-emitting diode (LED) indicators that convey information to the operator, such as positive electrical connection with the patient monitoring system and patient signal quality.

In yet another embodiment, a system can comprise an internal patient interface that is designed to collect sounds from within the peritoneal cavity. By way of example, the patient interface comprises a small diameter microphone catheter that is left in place after surgery has been completed, in similar manner to a drainage catheter. Such a patient interface may be particularly useful in cases in which the patient is obese and it is more difficult to obtain high-quality signals from the surface of the skin. To avoid passing current into the patient, the patient interface can comprise a laser microphone. In such a case, a laser beam is directed through the catheter and reflects off a target within the body. The reflected light signal is received by a receiver that converts the light signal to an audio signal. Minute differences in the distance traveled by the light as it reflects from the target are detected interferometrically. In alternative embodiments, the patient interface 68 can comprise a microphone that is positioned at the tip of the catheter.

As described above, it is noted that combinations of the system components are possible. For instance, the user interface could be used with the data collection device, if desired. All such combinations are considered to be within the scope of this disclosure.

As is indicated in FIG. 2, the device 72 generally comprises a processing device 74, memory 76, a user interface 78, and input/output devices 80, each of which is coupled to a local interface 82, such as a local bus.

The processing device 74 can include a central processing unit (CPU) or other processing device, such as a microprocessor or digital signal processor. The memory 76 includes any one of or a combination of volatile memory elements (e.g., RAM) and nonvolatile memory elements (e.g., flash, hard disk, ROM).

The user interface 78 comprises the components with which a user interacts with the device 72. The user interface 78 can comprise, for example, a keyboard, mouse, and a display device, such as a liquid crystal display (LCD). Alternatively or in addition, the user interface 78 can comprise one or more buttons and/or a touch screen. The one or more I/O devices 80 are adapted to facilitate communication with other devices and may include one or more electrical connectors and a wireless transmitter and/or receiver. In addition, in cases in which the device 72 is the data collection device, the I/O devices 80 can comprise a microphone 84. In certain other embodiments, the algorithms utilized in the systems of the invention are trained and learn noise mitigation without the use of a second microphone. This aspect of the invention can prevent the system/device from discarding data due to noise.

The memory 76 is a computer-readable medium and stores various programs (i.e., logic), including an operating system 86 and an intestinal sound analyzer 88. The operating system 86 controls the execution of other programs and provides scheduling, input-output control, file and data management, memory management, and communication control and related services. The intestinal sound analyzer 88 comprises one or more algorithms that are configured to analyze intestinal audio data for the purpose of predicting the likelihood of a patient developing GII. In some embodiments, the analyzer 88 conducts that analysis relative to correlation data stored in a database 90 and presents to the user (e.g., physician or hospital staff) a predictive index of GII risk. In some embodiments, the analyzer 88 identifies particular spectral events of interest (associated with the audio data from sounds within the patient, e.g., digestive sounds) using target signal parameters, signal-to-noise ratio parameters, and noise power estimation parameters. Decision tree analysis of the number of predictive spectral events during a specified time interval can then be used to communicate a high-, intermediate-, or low-risk of GII.

As will be appreciated, the invention described herein may be applied for predictive assessment of other potential life-threatening, conditions related to congestive heart failure ("CHF"), acute respiratory distress syndrome ("ARDS"), pneumonia, pneumothoraxes, vascular anastomoses, arterial aneurysm, and the other similar conditions, for which internal sounds related to the specific condition can be collected for analysis as described herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated herein.

What is claimed is:

1. A method for improved predictions of in vivo impairments and events in real time prior to clinical diagnosis and symptoms for post-operative management of gastrointestinal intolerance or impairment (GII) in surgical patients, wherein the method comprises:

receiving, by a system comprising one or more computers, training samples including a plurality of labeled raw audio samples obtained from subjects within a predetermined period within 12 hours following surgery and having a predetermined duration of approximately 4 minutes, the labeled raw audio samples being labeled according to post-operative, subsequent outcomes with respect to gastrointestinal intolerance or impairment (GII) collected from one or more subjects;

passing, by the system, each training sample of the training samples through a machine learning encoder and transforming each training sample into training data as a new representation of the collected plurality of labeled raw audio samples by calculating a Fast Fourier Transform (FFT) of the intestinal audio samples and generating mel-frequency cepstral coefficients (MFCC) from post-FFT samples to markedly reduce dimensionality of the data;

passing, by the system, the training data through a machine learning classifier to generate a classifier function, including applying, by the machine learning encoder, a misclassification cost algorithm and up-sampling rare classes corresponding to GII-positive outcomes to bias training toward detection of gastrointestinal intolerance or impairment (GII);

receiving, by the system, testing samples including a plurality of unlabeled raw audio samples comprising intestinal audio samples obtained from the one or more subjects within the predetermined period within 12 hours following surgery and having the predetermined duration collected from the one or more subjects;

passing, by the system, each testing sample of the testing samples through the machine learning encoder and transforming each testing sample into testing data as a new representation of the collected plurality of unlabeled raw audio samples by calculating the FFT of the intestinal audio samples and generating MFCCs from post-FFT samples to markedly reduce dimensionality of the data;

passing, by the system, the testing data through the classifier function to classify the testing data;

comparing, by the system, a predicted outcome to an actual outcome to measure performance of the classifier function and minimize false negatives and false positives;

adjusting, by a machine learning classifier of the system, generation of the classifier function based on the measured performance, including iteratively adjusting classifier parameters utilizing at least one of a neural network perceptron algorithm and a multiclass perceptron algorithm until a predetermined performance threshold is met, thereby providing a validated classifier function configured for improved prediction of gastrointestinal intolerance or impairment (GII);

receiving, by the system, collected audio data from an audio capture device configured to collect data from another subject with no pre-clinical diagnosed symptoms of gastrointestinal intolerance or impairment (GII) within the predetermined period within 12 hours following surgery;

passing, by the system, the collected audio data from the audio capture device through the machine learning encoder and transforming the collected audio data into new audio data as a new representation of the collected audio data by calculating the FFT of the collected intestinal audio data and generating MFCCs from post-FFT samples to markedly reduce dimensionality of the data;

passing, by the system, the new audio data through the classifier function to classify the new audio data and predict a likelihood of an in vivo impairment or event occurring prior to clinical diagnosis and clinical symptoms in the another subject with no pre-clinical diagnosed symptoms of gastrointestinal intolerance or impairment (GII); and providing the predicted likelihood via a user interface to clinical staff to guide post- operative management including timing of nasogastric tube removal, oral intake, or initiation of one or more interventions, or a combination thereof, to prevent or mitigate gastrointestinal intolerance or impairment (GII).

2. The method of claim 1, wherein a computer of the one or more computers comprises:

one or more processors, one or more non-transitory computer-readable storage mediums storing instructions comprising one or more algorithms that when executed by the one or more processors cause the one or more processors to perform one or more steps, a user interface, and one or more input/output devices, wherein each of the one or more processors, the one or more non-transitory computer-readable storage mediums, the user interface, and the one or more input/output devices is coupled to a local interface.

3. The method of claim 1, wherein the step of transforming reduces dimensionality of the data.

4. The method of claim 3, wherein the step of transforming comprises calculating a Fast Fourier Transform (FFT).

5. The method of claim 4, further comprising the step of transforming post-FFT samples.

6. The method of claim 5, wherein the step of transforming the post-FFT samples comprises the steps of:

i. mapping power spectrum of the post-FFT samples onto a mel scale;

ii. taking logs of power at each mel frequency of the mel scale;

iii. taking a discrete cosine transform of a list of the logs; and iv. obtaining amplitudes of each resulting spectrum, transforming raw signal into mel-frequency cepstral coefficients (MFCC) to markedly reduce dimensionality of the data.

7. A device for implementing the method of claim 1, wherein the device comprises the audio capture device configured to collect the data from the another subject with no pre-clinical diagnosed symptoms of gastrointestinal intolerance or impairment (GII) and predict the likelihood of the in vivo impairment or event occurring prior to clinical diagnosis and clinical symptoms in the another subject.

8. The method of claim 1, wherein the step of generating the classifier function includes at least one of:

applying, by the machine learning encoder, a misclassification cost algorithm to the plurality of labeled raw audio samples; and applying, by the machine learning encoder, up-sampling of rare classes to the plurality of labeled raw audio samples.

9. The method of claim 1, wherein the step of generating the classifier function includes:

screening, by the machine learning encoder, the plurality of labeled raw audio samples utilizing a plurality of machine learning algorithms; and selecting and retaining a validated machine learning algorithm of the plurality of machine learning algorithms, based on a comparison of a measured performance of each of the plurality of machine learning algorithms, as a validated and trained encoder component for the improved predictions of in vivo impairments.

10. The method of claim 1, further comprising:

after the comparing, adjusting the step of generating the classifier function by the machine learning classifier based on the step of comparing; and providing a validated and trained classifier function for the improved predictions of in vivo impairments.

11. The method of claim 10, wherein the step of adjusting includes at least one of:

adjusting the step of generating the classifier function, by the machine learning classifier, utilizing a probability threshold;

iteratively adjusting the step of generating the classifier function, by the machine learning classifier, utilizing a neural network perceptron algorithm; and adjusting the step of generating the classifier function, by the machine learning classifier, utilizing a multiclass perceptron algorithm.

12. The method of claim 10, wherein the step of adjusting is limited to a predetermined maximum number of adjustments.

13. The method of claim 1, wherein the plurality of labeled raw audio samples include intestinal audio samples obtained from subjects within the predetermined period within 12 hours following surgery.

14. The method of claim 13, wherein the predetermined period is within 12 hours of the surgery and the predetermined duration is approximately 4 minutes.

15. The method of claim 13, wherein the plurality of labeled raw audio samples include intestinal audio samples labeled according to post-operative, subsequent outcomes with respect to gastrointestinal intolerance or impairment (GII) and having the predetermined duration.

16. The method of claim 15, wherein the predetermined duration is approximately 4 minutes.

17. The method of claim 13, wherein the plurality of labeled raw audio samples include samples from subjects that experienced post-operative, subsequent outcomes with respect to gastrointestinal intolerance or impairment (GII) and are labeled according to the post-operative, subsequent outcomes.

18. The method of claim 1, wherein the method further comprises:

obtaining intestinal audio data from a plurality of subjects within the predetermined period within 12 hours following surgery, and segregating the intestinal audio data into the plurality of labeled raw audio samples and the plurality of unlabeled raw audio samples.

19. The method of claim 18, wherein the step of segregating includes one of:

randomly segregating the intestinal audio data into the plurality of labeled raw audio samples and the plurality of unlabeled raw audio samples; and segregating a first predetermined percentage of the intestinal audio data into the plurality of labeled raw audio samples and a second predetermined percentage of the intestinal audio data into the plurality of unlabeled raw audio samples.

20. The method of claim 19, wherein the first predetermined percentage is approximately 76% of the intestinal audio data and the second predetermined percentage is approximately 24% of the intestinal audio data.

21. A system for improved predictions of in vivo impairments and events in real time prior to clinical diagnosis and symptoms for post-operative management of gastrointestinal intolerance or impairment (GII) in surgical patients, wherein the system comprises:

a computer including one or more processors and one or more non-transitory computer-readable storage mediums storing instructions comprising the one or more algorithms that when executed by the one or more processors cause the one or more processors to perform steps including:

receiving the training samples including a plurality of labeled raw audio samples comprising intestinal audio samples obtained from one or more subjects within a predetermined period within 12 hours following surgery and having a predetermined duration of approximately 4minutes, the labeled raw audio samples being labeled according to post-operative, subsequent outcomes with respect to gastrointestinal intolerance or impairment (GII) collected from one or more subjects;

passing each training sample of the training samples through a machine learning encoder and transforming each training sample into training data as a new representation of the collected plurality of labeled raw audio samples by calculating a Fast Fourier Transform (FFT) of the intestinal audio samples and generating mel-frequency cepstral coefficients (MFCC) from post-FFT samples to markedly reduce dimensionality of the data;

passing the training data through a machine learning classifier to generate a classifier function, including applying, by the machine learning encoder, a misclassification cost algorithm and up-sampling rare classes corresponding to GII-positive outcomes to bias training toward detection of gastrointestinal intolerance or impairment (GII);

receiving the testing samples including a plurality of unlabeled raw audio samples comprising intestinal audio samples obtained from the one or more subjects within the predetermined period within 12 hours following surgery and having the predetermined duration collected from the one or more subjects;

passing each testing sample of the testing samples through the machine learning encoder and transforming each testing sample into testing data as a new representation of the collected plurality of unlabeled raw audio samples by calculating the FFT of the intestinal audio samples and generating MFCCs from post-FFT samples to markedly reduce dimensionality of the data;

passing, by the system, the testing data through the classifier function to classify the testing data;

comparing a predicted outcome to an actual outcome to measure performance of the classifier function and minimize false negatives and false positives;

adjusting, by a machine learning classifier of the system, generation of the classifier function based on the measured performance, including iteratively adjusting classifier parameters utilizing at least one of a neural network perceptron algorithm and a multiclass perceptron algorithm until a predetermined performance threshold is met, thereby providing a validated classifier function configured for improved prediction of gastrointestinal intolerance or impairment (GII);

receiving collected audio data from an audio capture device comprising an electronic stethoscope or microphone configured to collect data from another subject with no pre-clinical diagnosed symptoms of gastrointestinal intolerance or impairment (GII) within the predetermined period within 12 hours following surgery;

passing the collected audio data from the audio capture device through the machine learning encoder and transforming the collected audio data into new audio data as a new representation of the collected audio data by calculating the FFT of the collected intestinal audio data and generating MFCCs from post-FFT samples to markedly reduce dimensionality of the data;

passing the new audio data through the classifier function to classify the new audio data and predict a likelihood of an in vivo impairment or event occurring in the subject with no pre-clinical diagnosed symptoms of gastrointestinal intolerance or impairment (GII); and outputting the predicted likelihood via a user interface for use by clinical staff in adjusting post-operative treatment of the subject including timing of nasogastric tube removal, oral intake, or initiation of one or more interventions, or a combination thereof, to prevent or mitigate gastrointestinal intolerance or impairment (GII).

22. The system of claim 21, wherein the plurality of labeled raw audio samples include intestinal audio samples obtained from subjects within the predetermined period within 12 hours following surgery.

23. The system of claim 22, wherein the plurality of labeled raw audio samples include intestinal audio samples having the predetermined duration of 4 minutes.

24. The system of claim 22, wherein the plurality of labeled raw audio samples include samples from subjects that experienced post-operative, subsequent outcomes with respect to gastrointestinal intolerance or impairment (GII) and are labeled according to the post-operative, subsequent outcomes.

* * * * *